US006092660A

United States Patent [19]

Rune et al.

[11] Patent Number: 6,092,660

[45] Date of Patent: Jul. 25, 2000

[54] BLISTER PACK ARRANGEMENT

[75] Inventors: Simon Rune, Copenhagen, Denmark; Sven Eriksson, Hovås, Sweden

[73] Assignee: Astra Aktiebolag, Sodertalje, Sweden

[21] Appl. No.: 08/930,140

[22] PCT Filed: Jul. 4, 1997

[86] PCT No.: PCT/SE97/01218

§ 371 Date: Oct. 9, 1997

§ 102(e) Date: Oct. 9, 1997

[87] PCT Pub. No.: WO98/02131

PCT Pub. Date: Jan. 22, 1998

[30] Foreign Application Priority Data

Jul. 15, 1996 [SE] Sweden .................................. 9602781

[51] Int. Cl.[7] ............................ B65D 83/04; A61K 31/44

[52] U.S. Cl. ........................ 206/534; 206/459.5; 514/343

[58] Field of Search .................................... 206/528, 530, 206/570, 534, 535, 459.5, 461, 466, 807; 53/443, 492; 283/70, 900; 514/220, 343

[56] References Cited

U.S. PATENT DOCUMENTS 4,616,316 10/1986 Hanpeter et al. .
5,072,430 12/1991 Eckernas et al. ........................ 206/534
5,597,072 1/1997 Lieberman et al. .................... 206/534
5,747,512 5/1998 Keenan et al. .......................... 514/343
5,803,499 9/1998 Tung et al. ............................ 283/900
5,869,505 2/1999 Keenan .................................. 514/343

FOREIGN PATENT DOCUMENTS 41680 1/1971 Australia .
1939636 2/1970 Germany .

*Primary Examiner*—Paul T. Sewell
*Assistant Examiner*—Luan K. Bui
*Attorney, Agent, or Firm*—White & Case LLP

[57] ABSTRACT

A blister pack arrangement comprises at least one blister pack with individually openable blisters including a number of blisters containing placebo (placebo blisters), and a number of blisters containing an active pharmaceutical drug (drug blisters). Indicia means provides user information that indicates a predetermined sequence in which said blisters are to be opened during a trial period, said sequence being such that the placebo blisters are to be opened before the drug blisters. The blisters are not identifiable with each other either by sight or by said indicia means. An initially secret treatment code is to be broken after the trial period, revealing when in said sequence a switch is made from placebo to active drug.

21 Claims, 1 Drawing Sheet

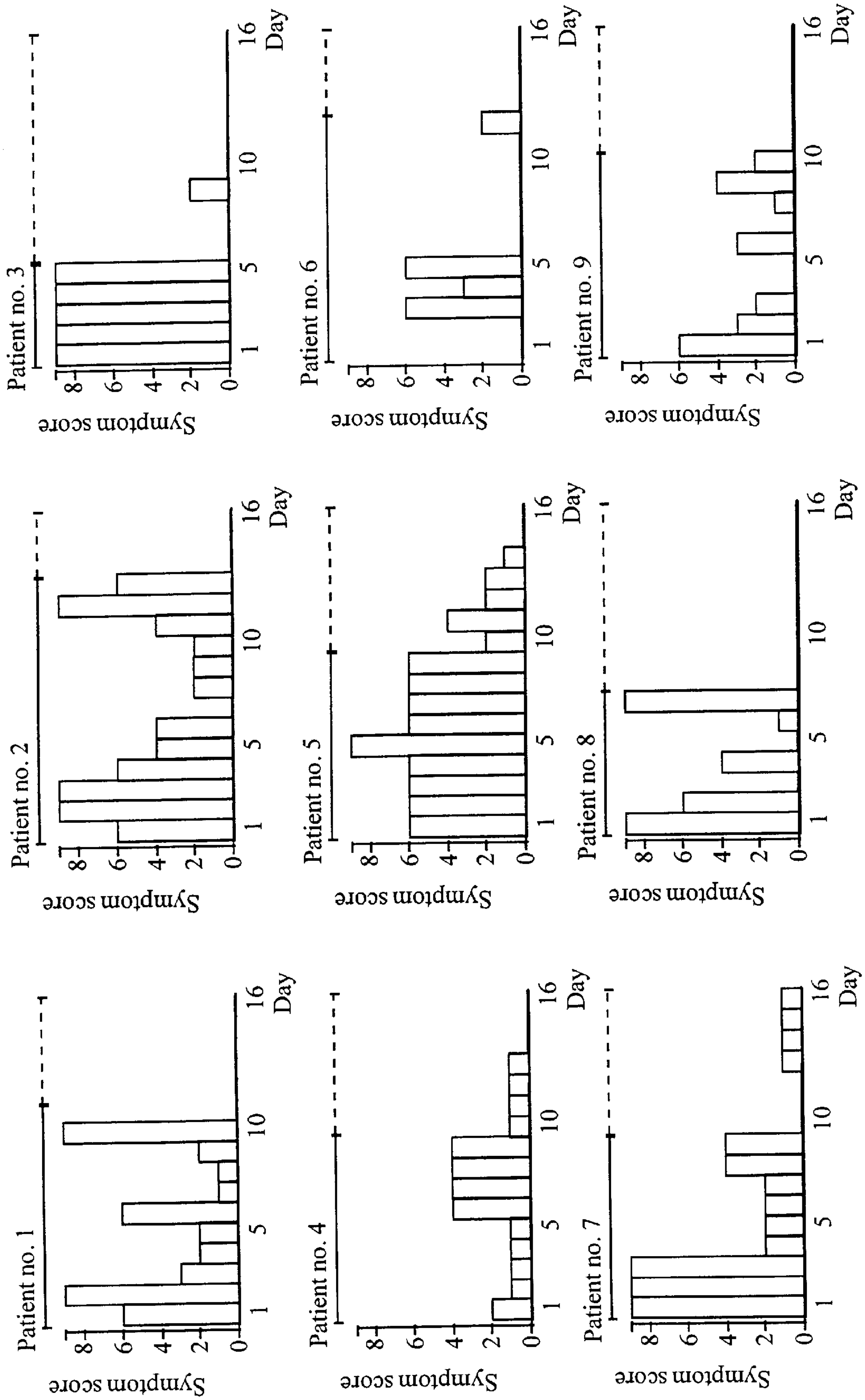
Patient no. 1
Patient no. 2
Patient no. 3
Patient no. 4
Patient no. 5
Patient no. 6
Patient no. 7
Patient no. 8
Patient no. 9
Symptom score
8
6
4
2
0
1
5
10
16
Day

BLISTER PACK ARRANGEMENT

TECHNICAL FIELD

The present invention find is applicable within the field of using placebo for judging whether an observed improvement in a patient's symptoms results from pharmacological treatment or a placebo effect, or is a spontaneous event. More specifically, the present invention relates to a blister pack arrangement for implementing a Single Subject Trial of a type referred to as a Random Starting Day Trial.

BACKGROUND OF THE INVENTION

For many conditions, such as dyspepsia, asthma, headache and arthritis, it is often difficult to judge whether an observed improvement in a patient's symptoms results from pharmacological treatment or a placebo effect, or is a spontaneous event. To overcome this problem; Single Subject Trials (N-of-1 trials) were designed. These have a long tradition of use in psychology and psychiatry, but the early studies were often non-randomised and the evaluation of the observations was largely subjective. In the 1980s, single subject trials were re-introduced to assist in decisions on a drug's efficacy in the treatment of an individual patient. The design of the trial was refined, and in the revised design the patient is given an active drug and placebo in randomised order in a double-blind cross-over manner for a series of consecutive periods (of up to 1 week). The judgement of the drug's efficacy is based on a comparison of symptoms during active treatment periods with those during placebo periods.

There are, however, some statistical problems and weakness associated with this design of trial. Inferential problems of the multiple cross-over design emanate from two sources: observations from adjacent periods are likely to be autocorrelated (i.e. more similar than observations that are more distant in time) and carry-over effects from the preceding period are not uncommon. Thus the basic and fundamental assumption of independence between observations that underlies most statistical methods is likely to be more or less violated, and there is an increased risk of significance tests and confidence intervals resulting in false conclusions.

Furthermore, a Single Subject Trial with multiple cross-over design is not suitable for testing the efficacy of drugs with a long duration of action (i.e. several days), because it necessitates the inclusion of wash-out periods, which prolongs the trial. The trial length may be critical for conditions with spontaneous variations in disease activity.

In an attempt to overcome these problems, a novel alternative, The Random Starting Day (RSD) trial, has been designed and briefly described in an abstract presented at the World Congress of Gastroenterology, Oct. 2–7,1994. According to said abstract the basic principle of the RSD trial is as follows: The patient starts on placebo and, on a randomly chosen day, switches to the active drug for the remainder of the trial period. The day for switching is randomly determined and varies between patients, and it is known neither to the patient nor the investigator or physician.

SUMMARY OF THE INVENTION

It is an object of the present invention to provide means for implementing an RSD Trial.

It is another object to provide means for implementing an RSD Trial for a group of patients.

It is yet another object to provide means for implementing an RSD Trial in an easy and cost-effective, but still reliable way.

It is still another object to provide such means for implementing an RSD Trial which the patient can start to use directly after delivery over-the-counter, without any need of action by a physician until the end of a trial period.

In view of these objects the invention provides a blister pack arrangement which comprises: at least one blister pack with individually openable blisters including a number of blisters containing placebo, referred to as placebo blisters, and a number of blisters containing an active pharmaceutical drug, referred to as drug blisters; indicia means providing user information that indicates a predetermined sequence in which said blisters are to be opened during a trial period, said sequence being such that the placebo blisters are to be opened before the drug blisters; said blisters being not identifiable with each other either by sight or by said indicia means; and an initially secret treatment code to be broken by the physician after the trial period, revealing when in said sequence a switch is made from placebo to active drug.

The blister pack arrangement according to the invention differs from conventional blister packs, containing but an active pharmaceutical drug for curing a patient, in that the primary field of application of the inventive blister pack arrangement is to investigate the efficacy of a drug in an individual patient.

According to a first embodiment of the invention, the arrangement comprises only one blister pack for the whole trial period of a patient. However, it is also envisaged that the arrangement may comprise more than one blister pack.

Thus, according to a second embodiment, the arrangement further comprises one or more placebo blister packs with placebo blisters only, wherein said sequence is such that said one or more placebo blister packs are to be opened before the above-mentioned "mixed" blister pack containing both placebo and drug blisters.

According to a third embodiment the arrangement further comprises one or more drug blister packs with drug blisters only, wherein said sequence being such that said one or more drug blister packs are to be opened after the above-mentioned "mixed" blister pack containing both placebo and drug blisters.

In practice, the embodiment to be chosen will depend on the length of the trial period, the number of blisters to be opened each day and the size of the blister packs as well of the blisters used. As a non-limiting, illustrative example the patient may be provided with, say, three blister packs for the trial period, namely a first pack with placebo blisters only, a second pack with a mix of placebo and drug blisters, and a third pack with drug blisters only.

Of course, the inventive feature that said blisters are not identifiable with each other either by sight or by said indicia means also applies to the above second and third embodiments, and combinations thereof. Independently of the number of blister packs actually used for one patient during a trial period, neither the patient nor the physician must be able to determine when in the sequence the "placebo/drug-switch" takes place. All blisters are therefore identical, and neither the indicia means, nor the layout of the blisters may give any information about where the switch will take place.

Preferably, the number of placebo blisters is randomly selected with the limitation that the number of placebo and drug blisters should have a predetermined sum.

In order to avoid any errors, the indicia means are preferably in the form of printed information or the equivalent directly on the blister pack. As an example thereof, the indicative information may comprise consecutive numbers adjacent to each blister, or only one indication where to start in case of e.g. a linear blister pack of roll-up type.

The initially secret treatment code preferably refers to the indicia means. As an example thereof, the treatment code for a specific trial may reveal that blister Nos. 1–7 included placebo, whereas blisters Nos. 8–16 included an active drug. Preferably, the code will be connected in some way to the blister pack in order to avoid errors or risk as mislaying the secret code. As an example thereof, the code may be provided on a back surface of the blister pack with a tamper-proof, peelable cover film preventing the code from being read in advance. Alternatively, the code may be disconnected from the blister pack and sent to the physician.

The above and other features of the blister pack arrangement according to the invention are set out in claims 1–15.

According to another aspect of the invention, there is provided a set of a plurality of blister pack arrangements according to the invention, each of which for use in a single RSD Trial, wherein the predetermined sequence in which the blisters are to be opened is the same for all of the blister pack arrangements in the set, but wherein each one of said blister pack arrangements in the set has a randomly selected number of placebo blisters. Such a set may be used for performing a RSD Trial on a group of patients. Preferably, the sum of placebo blisters and drug blisters is the same in each one of said plurality of blister pack arrangements.

Description of an RSD Trial and the Evaluation thereof

An inventive blister pack arrangement, or a set of such arrangements, may be used for implementing the RSD Trial described below.

The results of the trial performed on nine patients are illustrated in the diagrams in the attached drawing, wherein placebo is marked with a full line ("———") and omeprazole is marked with a dashed line ("-----"). The following description also includes an evaluation of the prognostic value of the trial, based upon results obtained with a potent acid inhibitory drug in patients with non-ulcer dyspepsia. It is also described how the predictive value of a positive response can be evaluated.

A Single Subject Trial is a tool for investigating the efficacy of a drug in the individual patient. It is designed as a multiple cross-over between active drug and placebo, and a response is defined as the identification by the patient of those periods using the active drug. Statistical problems are associated with this design. In particular, it is not suitable for testing drugs with a long duration of action.

As described above, in the RSD Trial the patient starts on placebo and, on a randomly chosen day, blindly switches to active treatment, which is continued for the remainder of the trial period. To this end, a blister pack arrangement according to the invention may be used. A symptomatic response, according to pre-defined criteria, registered within a predefined short period after the switch, is considered to be drug-induced.

An evaluation of the Random Starting Day Trial has been undertaken in patients with non-ulcer dyspepsia who were treated with omeprazole; the predictive value of a positive response within the first two days of active treatment was estimated to be 86%.

The model provides a useful means of estimating the predictive value of a positive symptomatic response.

When using the invention, the patient is provided with a blister pack arrangement according to the invention together with a diary card in a specified format for the daily recording of symptoms. Criteria for defining if and when a symptomatic response occurs have been predetermined. At the end of the trial period, the secret treatment code is broken by the physician. For patients in whom a symptom response occurs, the time relationship between the switch to active drugs and the relief of symptoms determines whether or not the symptom response should be considered as treatment-induced.

A first RSD Trial has been completed in patients with epigastric pain and no visible mucosal lesions at endoscopy. The aim was to identify patients with acid-related symptoms and the acid pump inhibitor omeprazole (40 mg once daily) was used as the active drug. The trial period was 16 days, starting with placebo and switching to omeprazole on a day between day 5 and day 14, so that the shortest possible time on placebo was 4 days (with 12 days on omeprazole), and the longest was 13 days (with 3 days on omeprazole). The patient recorded daily symptoms on a four-point Likert scale. A response was defined as a reduction of symptom score of at least 50% that continued until the end of the trial period. A response was considered treatment-induced if it took place within the first two days of active treatment.

Application of RSD Trials and Model Assumptions

RSD trials are intended for groups of patients in whom untreated symptoms have persisted for weeks or months, but who have also had intermittent periods of spontaneous a symptom relief. In these patients, the overall pattern of symptoms, when they occur, is stable but there are random day-to-day variations. In the RSD trial, there is one category of patients who respond to active treatment (e.g. those with an acid-related disease who respond to omeprazole treatment) and another category of patients who do not respond to active treatment (e.g. those with a non-acid-related disease).

The following specific model assumptions are made as a basis for the statistical evaluation of the outcome of RSD trials:

1. The probability of a persistent spontaneous response in untreated patients with an acid-related disease is the same as for untreated patients with a non-acid-related disease.
2. All patients with an acid-related disease respond to the switch to active treatment, e.g. omeprazole.
3. In patients with a non-acid-related disease, the pattern of symptoms is unaffected by active treatment. (Any symptom response seen after the switch to active treatment is spontaneous and coincidental.)

When the above assumptions 1–3 are fulfilled, it is known that:

in those patients who did not show a symptomatic response to the switch to the active drug, only patients with non-acid-related symptoms are found; and in the group of patients showing a symptomatic response at the time of switching to the active drug, some respond because they have acid-related symptoms, while others with non-acid-related symptoms experience, by chance, spontaneous symptom relief at this time.

The Predictive Value of a Negative Response

There is a direct implication in the second model assumption that is crucial for a correct understanding of the results of an RSD trial. As a consequence of the assumption that all patients with acid-related symptoms respond to the active drug, the predictive value of a negative response (i.e. lack of response) will always be 100%. The validity of this assumption should always be assessed. In our case, it is based on the fact that the active drug, omeprazole 40 mg once daily, decreases the 24 h intragastric acidity by 97%, on average. The assumption was tested further by subjecting nine patients with epigastric pain due to an endoscopially verified duodenal ulcer to an RSD trial. As shown in the diagrams in the drawing attached, all these patients experienced a symptomatic response. The response occurred spontaneously before the switch to omeprazole in patient No. 6, while in the other eight patients it occurred within the first two days of omeprazole treatment.

The Predictive Value of a Positive Response

The cause of symptoms cannot be evaluated in those patients who respond spontaneously before the switch to active treatment, because of the assumptions in the model. The basis for the evaluation of the positive predictive value of a response relating to the switch to active treatment is the group of patients who have not responded spontaneously before the switch. The number of patients in this group who respond to the switch is expected to give an overestimate of the proportion of patients with an acid-related disease.

This proportion of patients with an acid-related disease needs to be estimated as a first step in the calculation. It can then be used in the estimation of the positive predictive value. The estimation procedure is described in detail below under the heading "Statistical assumptions".

There were 123 patients in the trial. Table I shows, on a daily basis, the number of patients exposed to placebo and with no previous response. The estimated conditional probability of a spontaneous response on a given day is low. It varies between 0% and 6% per day with no systematic change seen during the trial period. The average, 3.2%, represents the best estimate of the probability of a spontaneous symptom response on any given day between day 5 and day 13. The life-table technique, which takes drop-outs into account, has been used to estimate the cumulative probability of a spontaneous symptom response. No assessment of whether or not the symptoms are acid-related can be made for patients responding spontaneously before switching to the active drug. The risk of a spontaneous response is therefore 12% for those switching on day 5 and 31% for those not switching until day 14 (Table I).

It is assumed that a treatment-induced response occurs within the first two days after the switch to active drug. The evaluation is, in principle, based on a comparison with the risk of a placebo response for the same two days. The estimated risk of such a spontaneous response now increases to an average of 6.2% (see "Statistical assumptions", page 14-). Overall, 32% of the patients responded during the first 2 days of active treatment (Table II).

Based on these two values, the proportion of true responders (i.e. patients with an acid-related disease) in the population as well as the positive predictive value of a symptom response within the first 2 days of active treatment is estimated as described below under the heading "Statistical assumptions". The prevalence of an acid-related disease in this study group was estimated to be 28% and the positive predictive value to be 86%.

DISCUSSION

The relatively simple design of the Random Starting Day trial and its high predictive value of a positive response makes it an obvious alternative to the widespread use of "empirical treatment", i.e. prescribing a drug and waiting for a symptomatic improvement during the following days. The positive predictive value found in this study, however, does not apply to another population with a different prevalence of an acid-related disease and another probability of a spontaneous symptom response. It is therefore of some interest to investigate the robustness of the method. Table III gives different theoretical values for the proportion of patients with a spontaneous response as well as the probability of a drug-induced response. Only the two extreme cases, with a daily incidence of placebo response as high as 7% or 10% and a proportion of patients with an acid-related disease as low as 10%, resulted in a low positive predictive value, 61% and 53%, respectively. In all the other cases considered, the positive value is 70% or higher.

The validity of the model assumption that all patients with an acid-related disease respond rapidly to active treatment depends on the effectiveness of the drug in eliminating the symptoms and their cause. In the present study, the aim was to identify acid-related symptoms in dyspeptic patients with no visible mucosal lesions in endoscopy, and it was assumed that a dose of omeprazole of 40 mg once daily would provide a sufficiently effective acid reduction to induce a response in acid-related symptoms. A study of those patients with known acid-related symptoms due to a duodenal ulcer shows that this assumption is reasonable, and the conclusion that a patient who does not respond to the switch to active drug seems fully justified. The purpose of an RSD trial is to evaluate the predictive value of a positive response. The model assumptions demonstrate both the strength and the weakness of the model. Despite its inability to estimate the predictive value of a negative response, the model provides a useful means of estimating the predictive value of a positive response.

This particular trial also highlights the necessity of using a drug that is very effective in eliminating symptoms in dyspeptic patients with no visible lesions in endoscopy. Otherwise the model assumptions would not represent a reasonable approximation to reality. Using a daily dose of 40 mg of omeprazole makes it reasonable to assume that the model assumptions are likely to be correct and, therefore, that a positive response has a high predictive value.

TABLE I

Number of patients on placebo and number responding spontaneously. Estimated daily and cumulative risk of spontaneous response.

| Day No. | 1 | 2 | 3 | 4 | 5 | 6 | 7 | 8 |
|---|---|---|---|---|---|---|---|---|
| Patients on placebo | 123 | 120 | 117 | 110 | 98 | 81 | 66 | 55 |
| Spontaneous responses | 3 | 3 | 7 | 2 | 6 | 3 | 1 | 1 |
| Estimated risk of response (%) | 2 | 3 | 6 | 2 | 6 | 4 | 2 | 2 |
| Cumulative risk of response (%) | 2 | 5 | 11 | 12 | 18 | 21 | 22 | 23 |
| Day No. | 9 | 10 | 11 | 12 | 13 | 14 | 15 | |
| Patients on placebo | 43 | 38 | 31 | 21 | 10 | 0 | 0 | |

-continued

| | | | | | | | |
|---|---|---|---|---|---|---|---|
| Spontaneous responses | 0 | 1 | 1 | 1 | 0 | 0 | 0 |
| Estimated risk of response (%) | 0 | 3 | 3 | 5 | 0 | — | — |
| Cumulative risk of response (%) | 23 | 25 | 28 | 31 | 31 | — | — |

Estimated average risk per day (day 5–13)=3.2%

TABLE II

The estimated conditional probability of a response within two days of the starting of active treatment.

| First day of active treatment | Patients at risk | Patients responding within two days | Estimated probability of response (%) |
|---|---|---|---|
| 5 | 10 | 4 | 40 |
| 6 | 11 | 5 | 46 |
| 7 | 12 | 3 | 25 |
| 8 | 10 | 3 | 30 |
| 9 | 10 | 2 | 20 |
| 10 | 5 | 3 | 60 |
| 11 | 6 | 2 | 33 |
| 12 | 9 | 5 | 56 |
| 13 | 10 | 3 | 30 |
| 14 | 10 | 0 | 0 |
| 15 | — | — | — |
| Total | 93 | 30 | 32.3 |

TABLE III

Positive predictive value (%) by proportion of patients with an acid-related disease and by risk of spontaneous response

| Risk of spontaneous response | Proportion with acid-related disease | | | |
|---|---|---|---|---|
| | 10% | 20% | 30% | 40% |
| 2% | 85 | 93 | 96 | 97 |
| 3% | 79 | 89 | 93 | 96 |
| 5% | 69 | 83 | 90 | 93 |
| 10% | 53 | 71 | 81 | 87 |

Statistical Assumptions

Off Treatment

The conditional probability of a spontaneous response on a specific day (given that the patient so far has not responded and remains on placebo treatment) is the same for patients with an acid-related disease and a non-acid-related disease.

From day X (the first possible day of active treatment) the conditional probability of a spontaneous response on placebo treatment remains constant over time.

The second assumption is due to the fact that some kind of regularity in the conditional probability over time is necessary for obtaining a reasonably precise estimate (a linear trend would be an alternative). Otherwise the probability would have to be estimated for each separate day. This would, even in a large clinical trial, result in imprecise and irregular estimates because of the small number of patients switching to active treatment on each individual day.

On Treatment

Patients with an acid-related disease: The conditional probability of a symptom response within the first two days of active treatment is 1.

Patients with a non-acid-related disease: The conditional probability of a symptom response is the same as for patients off treatment (on placebo) and is constant over time (i.e. only spontaneous responses occur)

The Following Notations Are Used a=the prevalence of acid-related disease ($0<a<1$)

1-a=the prevalence of non-acid-related disease p=the conditional probability of a spontaneous symptom response during a given day on placebo ($0<p<1$)

P=the conditional probability of a spontaneous symptom response within a 2-day period on placebo R=the conditional probability of a symptom response within two days of the starting of active treatment in a randomly selected patient.

Spontaneous Placebo Response

The conditional probability P as defined above is obtained from the 1-day probability p as:

$$P=p+(1-p)p \quad (1)$$

The first term represents the probability of a spontaneous response on the first day of the period considered, and the second term represents the probability that a spontaneous response does not occur on the first day but does occur on the second day. From Table I, $\hat{p}=0.032$, and therefore $\hat{P}=0.063$.

Prevalence of Acid-Related Disease

The conditional probability P of a response within the first two days of active treatment is a weighted mean of the probability of response in patients with an acid-related disease according to the basic assumptions (this probability is equal to 1), and the probability of response in patients with a non-acid-related disease (probability P, the same during placebo and active drug treatment).

Thus,

R=[proportion of patients with acid-related disease]×[probability of response in patient with acid-related disease]+

[proportion of patients with non-acid-related disease]×[probability of response in patient with non-acid-related disease]

that is $$R=a\times 1+[1-a]P. \quad (2)$$

Solving equation (2) gives the following expression for the prevalence a:

$$a=[R-P]/[1-P] \quad (3)$$

The insertion of the estimated 2-day spontaneous placebo response rate (0.063) and the average response rate within two days of the starting of active treatment (see Table II) yields an estimate, â, of the prevalence of acid-related disease:

$$\hat{a}=[0.323-0.063]/[1-0.063]=0.277$$

Positive Predicted Value

The positive predicted value of a response within the first two days of active treatment is defined as the conditional probability that a randomly chosen patient who responded within the first 2 days of active treatment actually has an acid-related disease. In this case, the positive predictive value, PPV, is given by the ration between the prevalence, a, of an acid-related disease and the probability R that a randomly chosen patient responds within the first two days of active treatment.

$$PPV=a/R$$

An estimate $\hat{P}PV$ is obtained by inserting the previous estimates of a and R:

$$\hat{P}PV=0.277/0.323=0.86$$

What is claimed is:

1. A blister pack arrangement comprising:

(a) at least one combination blister pack comprising a mix of individually openable blisters, wherein some of the blisters contain a placebo and the other blisters contain an active pharmaceutical drug, (b) indicia means providing user information that indicates a predetermined sequence in which said blisters are to be opened over a period of time, wherein, according to the sequence, the placebo blisters are opened before the drug blisters and the blisters are indistinguishable from each other by sight or by the indicia means; and (c) a code identifying that point in the sequence when a switch is made from placebo to active drug, wherein the code is secret at the beginning of the period and is broken at the end of the period.

2. The arrangement according to claim 1, wherein the number of placebo blisters is randomly selected.

3. The arrangement according to claim 2, wherein the total number of placebo and drug blisters is a predetermined sum.

4. The arrangement according to claim 1, further comprising at least one placebo blister pack comprising individually openable blisters containing placebo and wherein, according to the sequence, the placebo blister pack is opened before the combination blister pack.

5. The arrangement according to claim 1, further comprising at least one drug blister pack comprising individually openable blisters containing the active pharmaceutical drug and wherein, according to the sequence, the drug blister pack is opened after the combination blister pack.

6. The arrangement according to any one of claims 1–5, wherein some of the drug blisters contain a first active drug, while the other drug blisters contain a second, different active drug.

7. The arrangement according to any one of claims 1–5, wherein the indicia means is in the form of information printed on the blister pack.

8. The arrangement according to any one of claims 1–5, wherein the placebo blisters are located adjacent each other on the blister pack, and the drug blisters are located adjacent each other on the blister pack.

9. The arrangement according to any one of claims 1–5, wherein the code is connected to at least one blister pack.

10. The arrangement according to claim 9, wherein the code is provided on a back surface of at least one blister pack.

11. The arrangement according to any one of claims 1–5, wherein the code is provided separately from the blister packs.

12. The arrangement according to any one of claims 1–5, wherein the code is provided with tamper indication means arranged to indicate whether the code has been broken, and to prevent a user from restoring the code, when broken, to the initially unbroken state.

13. The arrangement according to any one of claims 1–5, wherein the active drug comprises an acid pump inhibitor.

14. The arrangement according to claim 13, wherein the active drug comprises omeprazole.

15. The arrangement according to any one of claims 1–5, wherein the period is 5–21 days.

16. A set comprising a plurality of individual blister pack arrangements according to any one of claims 1–5, wherein each blister pack arrangement has the same predetermined sequence in which the blisters are to be opened and a randomly selected number of placebo blisters.

17. The set of blister pack arrangements according to claim 16, wherein the total sum of placebo blisters and drug blister is the same for each blister pack arrangement.

18. The arrangement according to any one of claims 1–5, wherein the blisters are opened by a patient over the period for evaluating the patient's symptoms in response to the active pharmaceutical drug.

19. The arrangement according to claim 15, wherein the period of time is 7–16 days.

20. A tool for investigating the efficacy of a drug comprising the blister pack arrangement of any one of claims 1–5.

21. A method for evaluating whether an observed improvement in a patient's symptoms is due to a pharmacological treatment or a placebo effect, or is a spontaneous event, comprising the following steps:

(a) providing a blister pack arrangement comprising:

(1) at least one combination blister pack comprising a mix of individually openable blisters, wherein some of the blisters contain a placebo and the other blisters contain an active pharmaceutical drug, (2) indicia means indicating a predetermined sequence in which said blisters are to be opened by the patient over a period of time, wherein, according to the sequence, the placebo blisters are opened before the drug blisters and the blisters are indistinguishable from each other by sight or by the indicia means, and (3) a code identifying that point in the sequence when a switch is made from placebo to active drug, (b) supplying the blister pack arrangement and a diary card to the patient who opens the blister in accordance with the sequence and records on the diary card the occurrence and characteristics of symptoms over the period of time; and (c) breaking the code at the end of the period and establishing a time relationship between the switch to the active drug and the patient's symptoms as recorded in the diary.

* * * * *